United States Patent
Sponsel

(10) Patent No.: US 6,313,155 B1
(45) Date of Patent: Nov. 6, 2001

(54) COMPOSITION AND METHOD FOR TREATING MACULAR DISORDERS

(75) Inventor: William E. Sponsel, San Antonio, TX (US)

(73) Assignee: Board of Regents, The University of Texas System, Austin, TX (US)

(*) Notice: Subject to any disclaimer, the term of this patent is extended or adjusted under 35 U.S.C. 154(b) by 0 days.

(21) Appl. No.: 09/656,585

(22) Filed: Sep. 6, 2000

Related U.S. Application Data

(63) Continuation of application No. PCT/US99/04879, filed on Mar. 5, 1999
(60) Provisional application No. 60/077,092, filed on Mar. 6, 1998.

(51) Int. Cl.[7] ...................... A61K 31/425; A61K 31/385; A61K 31/135
(52) U.S. Cl. ................ 514/367; 514/439; 514/652
(58) Field of Search ........................ 514/439, 652, 514/367

(56) References Cited

U.S. PATENT DOCUMENTS

| | | | | |
|---|---|---|---|---|
| 4,797,413 | * | 1/1989 | Baldwin et al. | 514/432 |
| 5,153,192 | * | 10/1992 | Dean et al. | 514/226.5 |
| 5,789,435 | * | 8/1998 | Harris et al. | 514/439 |

\* cited by examiner

*Primary Examiner*—Raymond Henley, III
(74) *Attorney, Agent, or Firm*—Fulbright & Jaworski LLP

(57) ABSTRACT

A method and composition for treating macular disorders. A pharmologically effective amount of a carbonic anhydrase inhibitor is combined with a pharmologically effective amount of an ocular hypotensive agent sufficient to improve visual function.

106 Claims, 8 Drawing Sheets

CENTRAL 30-2 THRESHOLD TEST
THRESHOLD GRAYSTONE          THRESHOLD (dB)
10-31-96       GHT: Within normal limits
                                    27 27   27 19
                                 29 29 27   18 24 24
                                            (16)(26)
                              23 26 29 27   32 27 29 25
                                    (29)       (29)
                           25 28 30 31 31    32 35 26 26 24
                                    (29)        (29)
                           27 29 29 34 35    32 34 29 27 27
                           30 32 34 31 32    33 31 0 32 28
                                       (34)  (33)
                           20 28 30 31 31    30 27 28 32 28
                           (28)      (31)       (27)
                              27 28 29 30    29 29 30 28
                                 (28)              (26)
                                 27 28 29    28 28 26

Fovea: 36dB              FL: 5/25 XX   28 21   29 25
MD: +0.91 dB             PSD: 2.27 dB     (25)
02-12-97       GHT: Within normal limits
                                    27 23   23 19
                                 25 29 29   22 26 24
                                            (28)(26)
                              23 30 27 31   30 27 29 25
                                    (29)       (25)
                           27 28 30 31 33    30 27 26 26 24
                                    (29)        (29)
                           25 33 33 34 35    32 30 29 29 21
                           (25)                          (25)
                           24 30 32 33 32    31 39 0 30 28
                                       (34)  (33)
                           28 26 32 33 31    28 29 30 30 26
                                    (29)        (27)
                              25 30 27 30    31 27 26 26
                                 (28)              (28)
                                 27 28 29    28 26 22

Fovea: 36dB              FL: 4/25    26 25   25 25
MD: +0.66 dB             PSD: 2.33 dB   (25)
06-17-97       GHT: Within normal limits
                                    27 21   19 13
                                       (21) (19)
                                 17 29 29   22 20 24
                                 (23)
                              17 28 25 29   24 27 25 23
                              (21)  (27)       (29)
                           23 30 26 29 31    28 27 26 24 20
                                    (27)        (25)
                           27 29 31 32 29    34 28 25 29 25
                                            (34)
                           28 28 30 31 32    27 29 0 32 24
                                       (30) (29)
                           26 26 30 29 29    28 23 28 28 22
                                    (31)        (27)        (26)
                              23 28 27 28    25 27 28 28
                                 (28)              (28)
                                 27 28 27    24 26 20
                                                   (22)
Fovea: 25dB              FL: 2/26    26 23   21 23
MD: -1.01 dB             PSD: 2.64 dB

*FIG. 7*

COMPOSITION AND METHOD FOR TREATING MACULAR DISORDERS

This is a continuation application of international application number PCT/US99/04879, filed Mar. 5, 1999, which claims priority to U.S. provisional application No. 60/077,092, filed Mar. 6, 1998.

BACKGROUND OF THE INVENTION

1. Field of the Invention

Applicant's invention relates to a composition and method for treating certain ocular disorders and, particularly, macular edema and macular degeneration through the application of a topical carbonic anhydrase inhibitor and an ocular hypotensive agent or inotropic agents in an amount sufficient to improve visual function. Other macular disorders that can be treated are familial drusen, and macular disorders related to hypertension, angioma, papillitis, neuro retinitis (including Lebers stellate retinopathy) and other pigmentary retinal degenerative disorders.

2. Background Information

Macular edema is swelling within the retina in the critically important central visual zone at the posterior pole of the eye. An accumulation of fluid tends to distract the retinal neural elements from one another and from their local blood supply, creating a dormancy of visual function in the area. Usually, the process is self-limiting, but occasionally permanent visual disability results from macular edema Often times, the swelling may take many months to clear. The precise mechanism by which swelling is triggered is uncertain, but it is probable that certain natural metabolic toxins may play an important role in the disease process. Macular swelling may also follow the insertion of artificial lens implants and cataract surgery, particularly if there is a breach in the lens capsule which segregates the vitreous gel from the fluid-filled anterior chamber. Longstanding macular edema after cataract surgery is one of the most frustrating dilemmas in all of ophthalmology, and is remarkably common.

Macular edema is a common and alarming ocular problem, for which no useful form of therapy has been previously known.

Two types of cystoid macular edema are:
a. Those without vascular leakage: retinitis pigmentosa and other pigmentary retinal degenerative disorders, early stage macular hole, and choridal neovascularization; and
b. Those with vascular leakage: diabetic retinopathy; branch retinal vein occlusion; intermediate uveitis; and ideopathicretinaltelangiectasis.

Another even more common chronic condition, which has typically been presumed to be irreversible, is macular degeneration. Instead of fluid accumulating in the outer retina, hard accumulations of lipofuscin, a metabolic waste product, tend to accumulate between the photoreceptors and the villi of the retinal pigment epithelium. These accumulations gradually enlarge, and in their early pathologic phase create discrete accumulations known as drusen. The lipofuscin is believed to accumulate as a result of the breaking off of the photoreceptor elements. Shedding of the cellular components of the photoreceptors is constantly occurring in a healthy retina. Good retinal pigment epithelial metabolism generally ensures a rapid clearance of such catabolic by-products of vision. The accumulation of this waste material retards the interaction between the retina and the retinal pigment epithelium from which nutrients arrive and through which catabolites are cleansed establishing a vicious cycle of catabolite accumulation. The accumulations not only block metabolic transfer between the retina and retinal pigment epithelium; they actually continue to undergo photoresponsive metabolism, constantly wasting precious NADH reducing power with no benefit.

An improved local circulation or a stabilization of membrane pH gradients might retard or prevent the accumulation of lipofuscin and break the vicious cycle of progressive blockage and waste of metabolic products passing to and from the retina.

As drusen accumulate in number and begin to coalesce, vast areas of retinal photoreceptors may become permanently disengaged from their neighboring retinal pigment epithelial villi. The sections of retina so affected become blind. Sadly, the greatest propensity among the aging population is for drusen to accumulate in the very central area of vision, the macula. Macular degeneration is the most common cause of legal blindness in the United States and Europe. Acetazolamide, a carbonic anhydrase inhibitor, has been given orally to treat macular edema but, while helpful, produces unpredictable responses and characteristically generates many systemic side effects. Even with the lower doses used in treatment of macular edema, the experience of physicians using acetazolamide (Diamox®) has been far from gratifying, with the large proportion of patients failing to continue therapy because of poor drug tolerance.

Currently, zinc in tablet form is administered to treat macular edema, but is also not effective and lacks any substantive clinical scientific support.

Whereas macular edema typically affects only one eye, macular degeneration typically involves both eyes and is usually fairly symmetric in its presentation and progression. There is virtually no family of European heritage in America without some relative who has suffered progressive loss of vision in their latter years as a result of macular degeneration. The problem is on the rise, and will continue to mount as the baby boom generation progresses towards maturity.

Macuar disease afflicts a small area of the very central retina, an area critical for reading and color vision. This is an area not typically affected to any practical extent by the disease glaucoma, which tends to diminish the surround vision (that is, the peripheral retina). This distinction is important, since the present invention is based upon the novel use of drugs currently used in the treatment of glaucoma.

It is important to understand that the retina is essentially a specialized part of the brain, and its circulation is very tightly regulated. Blood flow through the brain is typically constant in healthy individuals, whether running a marathon or sleeping. Obviously, huge variations in the inflow pressure of carotid artery blood to the brain occur throughout a typical day, and the vasculature in the cerebral cortex responds by adjusting its resistance. This is accomplished by constriction or dilation of the vessels throughout the brain. If the cerebrospinal fluid pressure is increased, creating, in effect, a stiffer vascular bed in the cerebral cortex, the blood vessels in the brain dilate to reduce intrinsic resistance, maintaining constant blood flow. This process is called autoregulation.

Autoregulation in the retina is analogous to that found in the brain, so if intraocular pressure is reduced, circulation in the retina is not necessarily increased. This point is clearly illustrated as a coincidental feature of two of the cases provided herein. Hyperventilation (to blow off carbon doxide and thereby reduce circulation to all the intrinsic vessels of the eye), or treatment with latanoprost (increasing the flow of clear fluid out of the eye) both produced significant eye pressure reduction, but visual function was actually simultaneously diminished. In each instance, however, if dorzolamide was coadministered there was visual enhancement.

Dorzolamide's profound effect on circulation is clearly not the result of any effect the drug might have on eye pressure, but arises as a result of its interference with autoregulation in the eye. The drug produces greater vascular compliance (that is to say, vessels remain effectively wide open even when other factors present would tend to produce vasoconstriction). In practice, drugs which reduce eye pressure tend to produce minimal changes in circulation and vision, and may in certain instances actually diminish both. It was discovered, quite unexpectedly, that a range of agents which reduce eye pressure, even those known to produce visual decrease while reducing pressure, can have a powerfully positive effect on both circulation and vision when dorzolamide is coadministered. The effects of this combination therapy appear to be profound.

In essence, once dorzolamide has uncoupled the auto-regulatory system, which tends to balance changes in perfusion pressure with compensatory changes in intrinsic vascular tone, additional alterations in the perfusion pressure gradient (whether induced pharmacologically or by physiologic perturbation) are accompanied by a concomitant and corresponding change in retinal blood flow. There is no precedent for such a finding in the ophthalmological literature. The ability to uncouple autoregulation, manipulate perfusion pressure, and realize a corresponding physiologic effect opens up the potential for designing a range of specific treatments for a variety of retinal diseases.

SUMMARY OF THE INVENTION

U.S. patent application Ser. No. 08/445,899, filed May 22, 1995, and Ser. No. 08/806,866 filed Feb. 25, 1997, which are incorporated herein by reference, disclose treatment of macular disorders by increasing ocular blood flow via application of a topical carbonic anhydrase inhibitor (TCAI). The treatment disclosed there is independent of intraocular pressure.

The instant invention applies the discovery that macular disorders may be remarkably and unexpectedly more effectively treated if the TCAI is applied in combination with an ocular hypotensive agent. The likely mechanism for this result is that the ocular hypotensive agent permits an increased ocular perfusion pressure which in turn multiplies the beneficial increased blood flow effect of the TCAI. The improvement in vision or stabilization of the macular disorder caused by applying the TCAI and hypotensive agent in combination exceeds any expected improvements that would be caused by the TCAI and hypotensive agent if their effect was merely additive. Nothing in the existing literature on the treatment of glaucoma, nor in any anecdotal record, FDA submission or prior patent would have led one to expect the findings outlined below.

The present invention overcomes the problems of the prior art and provides an effective method for increasing retinal blood flow and particularly for treating macular disorders, most particularly macular edema and macular degeneration.

Briefly stated, the present invention comprises increasing vascular perfusion by applying a pharmacologically effective amount of a topical carbonic anhydrase inhibitor in combination with an ocular hypotensive agent or inotropic agent either to the eye or systemically. The present invention also comprises a method of treating macular edema and macular degeneration comprising the application to an affected eye of a topical carbonic anhydrase inhibitor in combination with an ocular hypotensive agent or inotropic agent, in an amount effective to ameliorate the macular edema or macular degeneration.

The instant invention provides an effective treatment for maintaining the health of the eye and effectively treating macular edema, macular degeneration, and other eye conditions by improved vascular perfusion in the retina of the eye.

This method for treating or preventing macular edema, macular degeneration, retinopathy of prematurity or any ocular disorder the etiology of which is clinically acknowledged to be partially or completely based upon inadequate vascular perfusion, comprises applying to the eye a pharmocologically effective amount of a topical carbonic anhydrase inhibitor in combination with an ocular hypotensive agent or inotropic agent. The carbonic anhydrase inhibitor may be a dorzolamide or brinzolanide and the ocular hypotensive agent or inotropic agent may be a beta blocker, adrenergic agonist, miotic, prostaglandin, and the like. The carbonic anhydrase inhibitor in combination with the ocular hypotensive agent or inotropic agent may be applied once daily to the eye or twice daily to the eye.

The carbonic anhydrase inhibitor may be administered as a 0.01–5%, preferably a 0.5 to 2% solution or suspension and the ocular hypotensive agent as a 0.001% to 6.0% solution or suspension in an ophthalmologically acceptable carrier. Such agents include, but should not be limited to beta blockers (betaxolol, timolol, optipranolol, levobunolol, metapranolol, carteolol, and the like), miotic agents (pilocarpine, carbachol, phospholine iodide, and the like), adrenergic agonists (ilopidine, brimonidine, epinephrine, dipivephrin, and the like), prostaglandin derivatives (latanoprost and the like), and related compounds directed toward the reduction of intraocular pressure, plus agents effective in the enhancement of carotid perfusion pressure, including a range of oral and sublingual systemic drugs intended to improve cardiac contractility or decrease carotid or ophthalmic arterial vascular resistance.

BRIEF DESCRIPTION OF THE DRAWINGS

FIG. 7 shows the visual fields of the patient of Example 3 prior to the fields of FIG. 5.

DETAILED DESCRIPTION OF THE PREFERRED EMBODIMENT

Figure 1A:
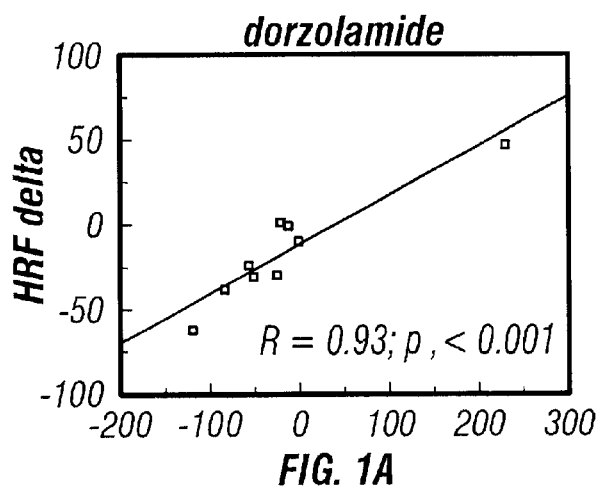
FIG. 1A is a correlation graph of retinal circulation as measured by Heidelberg Retinal Flowmetry (HRF) with dorzolamide.

The instant invention is grounded on the discovery that increasing vascular perfusion in the retina of the eye is a safe and effective way to maintain the health of the eye and to treat an ocular disorder which is based on inadequate vascular perfusion such as macular edema and macular degeneration. While the precise theory is not completely understood, it is believed that improved (i.e., increased) vascular perfusion in the retina of the eye greatly improves optic nerve health which, in turn, effectively combats macular edema and macular degeneration and other ocular disorders.

Circulation in the retina is highly pH-dependent. Studies in which various gases are introduced via the respiratory system into the blood stream clearly demonstrate that as the $CO_2$ level increases and pH decreases, circulation to the retina typically increases by upward of 40% from the baseline level observed during breathing of atmospheric air. Conversely, breathing pure oxygen produces a profound decrease in circulation in the retina. This latter response may be in part responsible for the disease process known as retrolental fibroplasia, or retinopathy of prematurity, which causes total or partial blindness in many premature infants.

The therapeutic use of oxygen in the treatment of neonatal premature infants may thus lead to blindness by inducing maldevelopment of the retinal arterial tree. It is very likely that this developmental flaw is promoted by vasospasm in the retinal vasculature. Very premature infants may develop similar problems when exposed to atmospheric levels of oxygen before their ocular tissues are ready.

It has been found that a safe and effective way to increase vascular perfusion in the retina of the eye is the application thereto of a TCAI.

TCAIs are well known for use in lowering intraocular pressure in treating glaucoma. Specific examples are acetazolamide, methazolamide, dorzolamide, pharmacologically active salts thereof and the like. These and other TCAIs are set forth in U.S. Pat. Nos. 4,386,098; 4,416,890; 4,426,388; 4,797,413; and 5,153,192; and are specifically incorporated herein by reference. Of these, dorzolamide and brinzolamide are preferred.

The TCAI are aromatic sulfonamides and can be used in the form of solutions, ointments, gels, or other topical ophthalmic preparations prepared with conventional amounts of conventional pharmacologically acceptable carriers, excipients, preservatives, and buffering agents conventionally used in preparing topical ophthalmic preparations.

Dorzolamide hydrochloride is a topically applied carbonic anhydrase inhibitor with a well established ocular hypotensive action. The drug is a powerful inhibitor of carbonic anhydrase in the ciliary epithelium, and is believed to have a similar effect on the anatomically contiguous neuroretina and its pigment epithelium. As such, the drug sequesters $CO_2$ and effects a reduction in pH within or adjacent to the retinal and choroidal vascular beds. Human experimental results show that dorzolamide may selectively enhance visual function and retinal perfusion.

Ocular circulation, like that of the cerebral cortex, is strongly influenced by ambient carbon dioxide. An increase in $CO_2$ in the blood is associated with an increase in retinal blood flow. Carbonic anhydrase is a ubiquitous and highly active enzyme which is responsible for $CO_2$ transfer and metabolism. Dorzolamide's efficacy in reducing intraocular pressure results from its ability to exceed a threshold of >99% enzyme inhibition at the level of the ciliary body, the site of aqueous humor production. Thus, sustained uveal penetration of the drug is required for any ocular hypotensive effect. Vascular responsiveness to $CO_2$, which is a more graded phenomenon, would be expected in tissues adjacent to the ciliary body, with potentiation of both perfusion (via vasodilation) and oxygen transfer (via the Bohr effect), since carbonic anhydrase is present throughout the uveal system and retinal pigment epithelium.

It will be evident that the amount of TCAI in the ophthalmic preparation can vary widely dependent mainly upon the age of the patient and type of ocular disorder. Effective amounts of the TCAI can vary from a 0.01 to 5% solution, preferably 0.5 to 2%.

In like manner, treatment will vary from 1 to 2 or more topical applications daily dependent mainly on the severity of the ocular disorder being treated.

The invention will be further described in connection with the following example which is set forth for purposes of illustration only.

EXAMPLE 1

Twelve consenting healthy adults (5 males and 7 non-pregnant, non-lactating females) all having intraocular pressures below 21 mm Hg and symmetric cup/disc ratios of 0.4 or less, were recruited for study under an institutional review board approved protocol. General exclusion criteria comprised (1) history of any systemic disease such as hypertension, diabetes, asthma, or vascular disorders, (2) pregnant or nursing women, or women planning a pregnancy, (3) participation in any drug research study within 30 days prior to entry into this study, or concurrent participation in any other research study, (4) chronic alcohol abuse, chronic drug abuse, concurrent tobacco use in any form, or use of illicit drugs, (5) drug therapy of any kind (including aspirin or platelet-active agent) within 2 weeks of entering the study, (6) any clinically significant acute health exacerbation (e.g., viral infection), recurrent or newly diagnosed condition or dysfunction which has not been stabilized or might require treatment of any kind, (7) any hematologic abnormality, and (8) history of hypersensitivity to sulfonamide drugs. Ophthalmic exclusive criteria were: (1) use of contact lenses within 12 hours of study entry, (2) any history of intraocular disease, (3) any active external ocular disease, infection, or uveitis, (4) corneal abnormalities, (5) asymmetry of intraocular pressure of more than 5mm Hg between eyes, (6) gonioscopic evidence of angle narrowing, (7) ocular or visual symptoms, including photophobia, photopsia, metamorphopsia, diplopia, or transient visual loss, (8) history of hypersensitivity to any topical ocular agent, (9) media opacities, (10) corrected visual acuity worse than 20/25 in either eye, and (11) astigmatism of >1.5 diopter in either eye.

The study was of double-masked, placebo-controlled, single-center, crossover design, to assess the effects of carbon dioxide on the visual function of 12 healthy adults, and to observe for any modulating effects of 2% dorzolamide under conditions of normal breathing, physiologic hypercapnia (with accompanying carbon dioxide tissue loading), followed rapidly by physiologic hypocapnia. Inclusion and exclusion criteria were rigidly enforced, and there was no subject attrition throughout the study.

Identical 5 ml ocumeter bottles containing either dorzolamide 2% or placebo were provided to each subject according to a randomized allocation schedule, the code of which was not revealed until the study was complete. Treatment was applied, one drop three times daily, to the right eye only. Six subjects received dorzolamide for 4 days, followed by a two-week washout period and then 4 days of placebo; six subjects received placebo eyedrops for 4 days, and a two-week washout followed by 4 days of dorzolamide.

A pre-study examination was conducted on each subject within 7 days of study entry during which the following was documented: ophthalmic and general history, visual acuity, external slit lamp examination, tonometry by pneumotonometer (mentor), dilated ophthalmoscopy, Humphrey 10-2 visual field, NeuroScientific 8010 two-alternative forced choice staircase contrast sensitivity testing (1 and 4 cycles per degree vertical sinusoidal gratings; square wave temporal modulation at 7.5 Hz presented on a black and white monitor, subtending 7.5 degrees at the 1.22m viewing distance fixed by a chin-head rest; 82 $cd/m^2$ space-averaged luminance at the screen), blood pressure, and heart rate. Blue field entoptic perimacular leukocyte velocity and density, scanning laser video fluorescein angiography, and Heidelberg scanning laser retinal flowmetry were also performed for related studies. All females of childbearing potential performed B-HCG pregnancy testing, and all were found to be negative.

Qualifying subjects were instructed in eyedrop application technique, and instilled one drop of study medication to the right eye at 8:00 a.m., 4:00 p.m., and at bedtime each day throughout the study period. At 9:00 a.m on day 2 of each study phase, contrast sensitivity was measured in both eyes. At 9:30 a.m., subjects commenced inhaling a mixture of 5% $CO_2$ in air through a sealed mouthpiece on a Rudolf valve system from a single premixed tank until the end-tidal $CO_2$ level was 15+/−2.5% above the starting level for at least 15 minutes. Blood pressure, pulse, and contrast sensitivity at the two spatial frequencies were measured while the subject continued to breath the gas mixture, followed by measurement of intraocular pressure. Subjects then commenced hyperventilating room air to the beat of a metronome until the $CO_2$ of their expired air was 15+/−2.5% below the initial baseline value for 15 minutes. All of the aforementioned measurements were obtained as the subject continued to hyperventilate.

On day 2, together with bilateral contrast sensitivity testing, each subject underwent studies of midperipheral retinal microcirculation in both eyes using the Heidelberg retinal flowmeter, avoiding any visible vessels, as described elsewhere. Similarly, each subject underwent, in the treated eye only, video fluorescein angiography using the Scanning Laser Ophthalmoscope (Rodenstock/Canon), to determine arteriovenous passage time (AVP; determined by finding the difference between the time of appearance of the dye in the peripapillary retinal arterioles and its reappearance in their corresponding veins) and capillary transit velocity (CTV; calculated by timing the passage of hypofluorescent particles through perifoveal capillaries).

On day 3, having continued the topical treatment three times daily to the right eye, each subject underwent perimacular leukocyte velocity and density studies in both eyes using the Oculix Blue Field simulation technique. Three sets of circulatory measurements were obtained under baseline (9:00 a.m.), $CO_2$ supplementation (9:45 a.m.) and hyperventilation (10:30 a.m.) conditions, as above, with the other concomitant physiologic measures and intraocular pressure also being monitored. At the conclusion of the study, subjects were instructed to discontinue topical treatment for 2 weeks, and were scheduled to return for an identical series of studies while using their second phase masked topical agent. Subjects were instructed not to use any ophthalmic or systemic medications during the washout period. A detailed protocol for monitoring and recording any adverse experiences, with appropriate case report forms, was employed throughout the study, no significant adverse experiences were encountered throughout the study.

Upon completion of both phases in all 12 subjects, statistical analysis was carried out to determine whether circulatory measures differed (under normal breathing conditions, hypercapnia, or hyperventilatory hypocapnia) while subjects were receiving dorzolamide from when they were receiving placebo. Similar comparisons were made between the treated right eye and untreated left eye. In addition, correlation studies were performed to elicit any significant associations which might exist between ocular perfusion and intraocular pressure changes. Comparisons were by standard 2-tailed t-test, and correlations by obtaining Pearson R values and Spearman Rank correlation probability analysis.

Figure 1B:
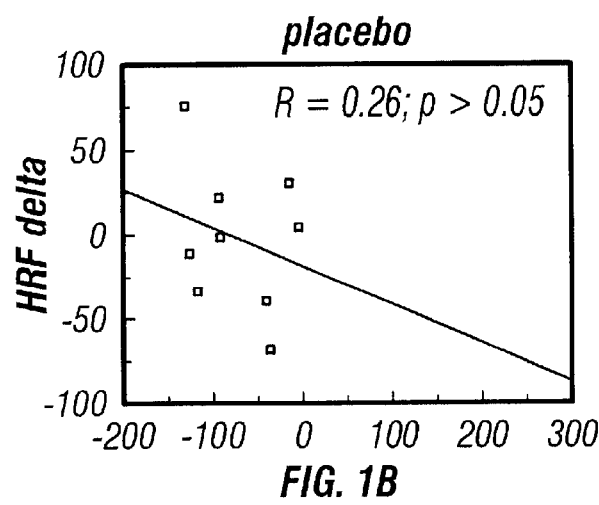
FIG. 1B is a correlation graph of retinal circulation as measured by Heidelberg Retinal Flowmetry (HRF) with a placebo.

It is known from prior analysis that dorzolamide enhances visual function and that vision responses are closely associated to retinal circulation (HRF in FIG. 1A and FIG. 1B) when the drug is present, but not in its absence. Mean intraocular pressure did not differ significantly with either dorzolamide or placebo treatment from pretreatment baseline values among these healthy, tonometrically normotensive subjects.

Figure 2:
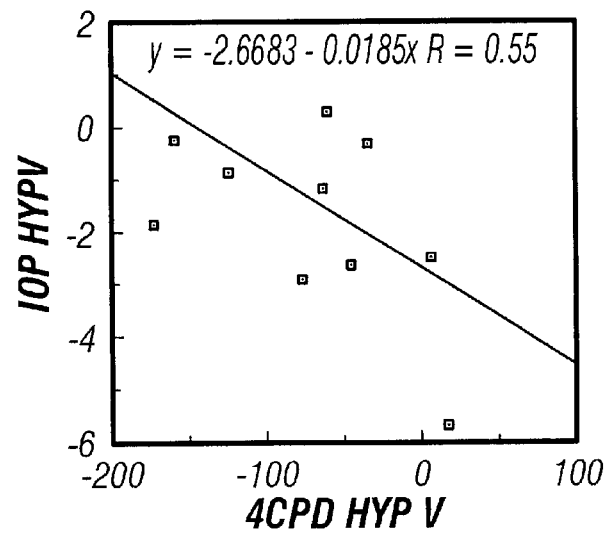
FIG. 2 is a correlation graph of IOP (hyperventilation) versus 4 cpd contrast sensitivity.
Figure 3:
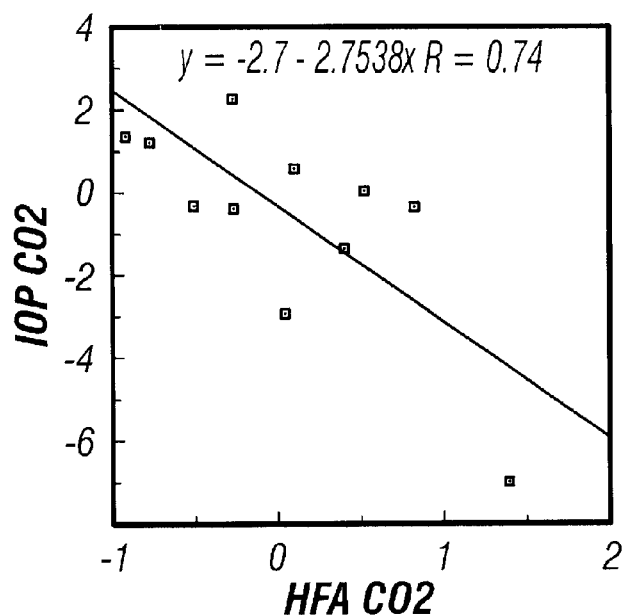
FIG. 3 is a correlation graph of IOP (hypercapnia) versus Humphrey Visual Field (HFA).

A more detailed analysis of study data discloses a series of second order associations not previously known to exist between the extent of intraocular pressure change and visual function during dorzolamide therapy (FIG. 2 and FIG. 3). These findings are most unexpected. Variable intraocular pressure responses arose among individuals in the study population under both hypercarbia and hyperventilation, the latter condition tending to result in both IOP and visual decrease among nearly all subjects.

Any effect dorzolamide may otherwise have exerted on the intraocular pressure per se among these normal eyes was overwhelmed by intraocular pressure effects of the gas perturbations. Yet, despite the absence of any significant drug-induced ocular hypotensive response, a series of remarkable secondary associations involving intraocular pressure changes, induced by the respiratory maneuvers, emerged upon close examination of the correlation data, but only when dorzolamide was present. As with the previous visual function analysis, no evidence was noted in the perfusion studies of any systemic pharmacologic crossover effect of topical dorzolamide to the nontreated fellow eye.

It should be understood that the eye has two largely independent circulatory systems, retinal and uveal. The retinal circulation accounts for only 2% of total eye circulation, but this 2% is critical to the health of the eye's "wiring" to the brain, i.e., the 1.2 million axons which make up the nerve trunk known as the optic nerve. The cell bodies containing the genetic material and metabolic machinery for these "wires" are all located in the inner layer of the retina, and derive virtually all their energy supply from the locally autoregulated retinal circulation. Any significant compromise to the retinal circulation is typically accompanied by visual loss.

In contradistinction, the majority of the eye's inner circulation passes through the uveal system, a spongelike, erectile tangle of vessels which lies behind the retina and its pigment epithelium. This vascular bed provides a rich supply of nutrients to the metabolically active photoreceptors of the outer retina, and the pigment epithelium which supports them. Moreover, this seemingly excessive blood supply acts as a heat sink to absorb thermal energy from focused light which could otherwise damage neural tissues.

The choroidal circulation, the part of the uveal vascular bed lying directly behind the retina, has some local regulation characteristics, but is also supplied with autonomic nerves capable of producing major changes in circulatory volume in response to stimuli—not necessarily even generated in the eye itself In healthy eyes, because of the choroid's relative abundance of vessels, fairly large changes in choroidal blood flow may be accompanied by minimal visual function change. However, since the uveal circulation comprises a significant portion of the ocular volume, a substantial drop in choroidal blood flow is generally accompanied by a significant decrease in intraocular pressure. Thus, during hyperventilation, when the natural vasodilator carbon dioxide is blown off, both choroidal and retinal circulation decrease in tandem, and visual function correspondingly diminishes. Typically, among the study group, an individual with a large intraocular pressure decrease would have a very large visual function deficit during hyperventilation.

Administration of dorzolamide, which is known to penetrate rapidly to the retina, would be expected to effect the sequestration of carbon dioxide in the back of the eye by blocking the enzyme responsible for its clearance from both the retina and choroid. The very volume of the local circulation in the choroid would be expected to clear the drug from that tissue more rapidly than from the retina. Thus, during hyperventilation the relative effects on vascular tone of dorzolamide would be expected to be greater in the retina than within the choroid, all other factors being equal. The independent autonomic nerve supply to the choroid allows its vessels to constrict in response to elimination of carbon dioxide throughout the body, while retinal blood flow is dictated by local changes only. Thus, despite dorzolamide therapy, hyperventilation still produces an introcular pressure decrease as a consequence of uveal vasoconstriction, since that system comprises the majority of the ocular circulatory volume.

Individuals with a large pressure drop, who tended to have the greatest visual loss during placebo treatment, produced large pressure drops during dorzolamide therapy, but had much more positive visual function responses. In essence, their relaxed retinal vasculature was able to exploit the choroidal vasoconstriction and accompanying pressure reduction in the eye, with improved perfusion pressure producing a noncompensated retinal circulation increase. This study evidenced that a physiologic stimulus classically associated with pressure reduction and visual loss could, in the presence of a TCAI, actually produce visual benefit.

Dorzolamide treatment in Example 1 was associated with a stabilization of retinal perfusion during both hyper- and hypocapnia. Scanning laser arteriovenous passage time and capillary flow velocity data both reveal an apparent modulating effect of dorzolamide on perfusion deficits observed during placebo treatment, with both $CO_2$ imbibation and subsequent hyperventilation. Moreover, parity of responses was noted to exist between visual function and retinal perfusion. Similar findings were obtained with both blue field entoptic and Heidelberg retinal doppler flowmetry, which measured relative changes in microcirculation in the perimacular and midperipheral retina, respectively.

A pronounced association was also seen to exist between the absolute values for perifoveal contrast sensitivity (4 cpd) and retinal microcirculation during hyperventilation during dorzolamide treatment which was absent during placebo administration. The same phenomenon was observed with blue field entoptic measurements. In dorzolamide treated right eyes, blue field velocity was significantly associated with contrast sensitivity at 4 cpd during hyperventilation (ANOVA R=0.58; P=0.05), but no such association was observed in the non-treated left eyes (R=0.00; P=0.99) or placebo treated right eyes (R=0.09; P=0.77). In no instance was any significant association observed between perfusion and visual function during placebo treatment, whether considered in absolute terms or as a change from baseline.

An additional physiologic phenomenon noted during this study may be of considerable potential relevance to our understanding of the $CO_2$ circulatory link in the retina. Using high speed video angiography with the Rodenstock/Canon scanning laser ophthalmoscope, the changes elicited by first breathing $CO_2$ enhanced air, following immediately by hyperventilation were observed. Arteriovenous passage time was monitored at the largest venules, one bifurcation from the optic nerve, and also at the smallest venules, equidistant from the disc. The former fill more slowly than the latter. During $CO_2$ breathing, arteriovenous passage time was significantly decreased in both large (p=0.005) and small (p=0.008) vessels. Upon hyperventilation, the large vessel filling rate returned to baseline, as expected (FIG. 2). However, the small vessels responded in an inverse manner, filling even more rapidly than during $CO_2$ breathing (FIG. 3). A similar dual response of large and small vessels to $CO_2$ has been observed in the brain, as discussed below.

Carbon dioxide, a ubiquitous and relatively benign product of human catabolism, promotes local vascular perfusion, facilitating its clearance and that of other waste products, and restoring nutrients to metabolically active tissue. The level of carbon dioxide in all tissues is dependent upon both metabolic and respiratory factors, and enzymes with extraordinarily high specific activity, the carbonic anhydrases, facilitate its movement between cells. Inhibitors of these enzymes tend to sequester carbon dioxide and thereby accentuate the endogenous effects of the gas on regional metabolism and blood flow.

The upward and downward changes in endogenous carbon dioxide induced experimentally are those a typical adult might naturally engender breathing beneath bedcovers or rapidly climbing stairs, respectively. The Dorzolamide treatment was associated with a stabilization of retinal perfusion during both hyper- and hypocapnia. Concerted responses were noted to exist between visual function and retinal perfusion under each breathing condition. A strong association between hyperventilatory perifoveal contrast sensitivity and retinal microcirculation noted during dorzolamide treatment was absent during placebo administration.

Similar findings have been obtained among a different study population receiving dorzolamide during hyperventilation without $CO_2$ preloading. Humphrey mean deviation (MD) values, under normal baseline breathing conditions, were significantly higher during dorzolamide treatment than during placebo treatment, and remained positive on dorzolamide and negative on placebo during $CO_2$ supplementation. Contrast sensitivity to a 30 Hz temporally-modulated 4 cpd sine wave grating decreased significantly with $CO_2$ supplementation during placebo treatment (p=0.006), but showed no change from baseline values during dorzolamide treatment. The decrease in contrast sensitivity to the 1 cpd pattern during $CO_2$ supplementation more than doubled during hyperventilation during placebo treatment, but remained the same with dorzolamide treatment.

Many significant correlations were seen between the visual and perfusion changes induced by shifts in end-tidal $CO_2$ among these normal subjects, but only when dorzolamide was in use. One striking example was the strong association between the change in Heidelberg flowmetry from baseline breathing to hyperventilation, and the accompanying shift in contrast sensitivity for the spatial frequency 4 cpd. This association was absent during placebo treatment. A similar phenomenon was observed in a separate study group.

Thus, in view of the unexpected associations observed between visual function and the drug-independent intraocular pressure shifts induced by respiratory maneuvers, the hypothesis was pursued that combination with more neutral agents of intraocular pressure reduction might effect even greater circulatory and visual increase.

An array of pharmacologic agents presented themselves as options for combination therapy, and several of these have been tested, as outlined below. It was subsequently confirmed that a combination of a TCAI with an ocular hypotensive agent in a 0.001–3% solution or suspension (or inotropic agent) will significantly enhance visual function in a manner heretofore unsuspected.

While dorzolamide appears to enhance visual function in normal subjects under normal conditions, and prevent visual decrease during perturbations of systemic carbon dioxide levels, it now has been found that combination with an additional ocular hypotensive agent such as a beta-blocker or the like greatly enhances the effect. During hypercapnia, the most pronounced modulating effect of dorzolamide was seen with the higher spatial frequency 4 cpd contrast pattern, which would be detected at the lowest threshold near the fovea. With ensuing hypocapnia, the modulating effect of dorzolamide on visual depression was seen most prominently with the lower spatial frequency I cpd contrast pattern, which would be detected at the lowest threshold peripheral to the fovea.

Hypocapnia is associated with decreased retinal perfusion. This perfusion decrease occurs despite a concomitant decrease in intraocular pressure, which would otherwise by definition, in the absence of other factors, increase retinal perfusion. Thus, the decrease in retinal sensitivity which accompanies hyperventilatory hypocapnia is clearly the consequence of factors which are neither provoked nor adequately compensated by aqueous hydrodynamic factors. The correlation analysis did not reveal any obvious association between pressure change and visual function change. The significantly greater degree of pressure reduction associated with dorzolamide therapy during hyperventilation may, however, be reasonably postulated to have a role in its observed visual protective effect under that condition.

Dorzolamide hydrochloride in combination with an ocular hypotensive or inotropic agent can enhance visual function in normal human eyes, under a range of physiologic conditions, via mechanisms which may be independent of or additive to the drug's known ocular hypotensive action.

EXAMPLE 2
(Coadministration of TCAI with Latanoprost, a Topical Prostaglandin Derivative)

Latanoprost (Xalatan®) is a recently-released drug with a unique mechanism of action for reducing intraocular pressure. The drug greatly increases the outflow of aqueous humour from the eye through a pathway which normally acts as a minor accessory outflow pathway. Latanoprost's intrinsic effects on ocular circulation remain unknown, but the drug is capable of effecting substantial reductions of intraocular pressure, even in eyes which have a normal pressure level at baseline.

An experiment was conducted in which measurements of visual function and perimacular retinal circulation were obtained on normal eyes: 1) at baseline, prior to any drug administration, 2) after 24 hours administration of three-times daily dorzolamide to the right eye only, and 3) after an additional 24-hour period of right eye treatment with dorzolamide at the same dosing rate, together with single bedtime applications of latanoprost to both eyes.

Intraocular pressure was not significantly changed in either eye on day 2, and was decreased by >30% on day 3 in both eyes. Perimacular leukocyte velocity (circulation in the reina near the macula) had increased to a supranormal level in the right eye only on day 3, with no other major differences from baseline in either eye.

Figure 4:
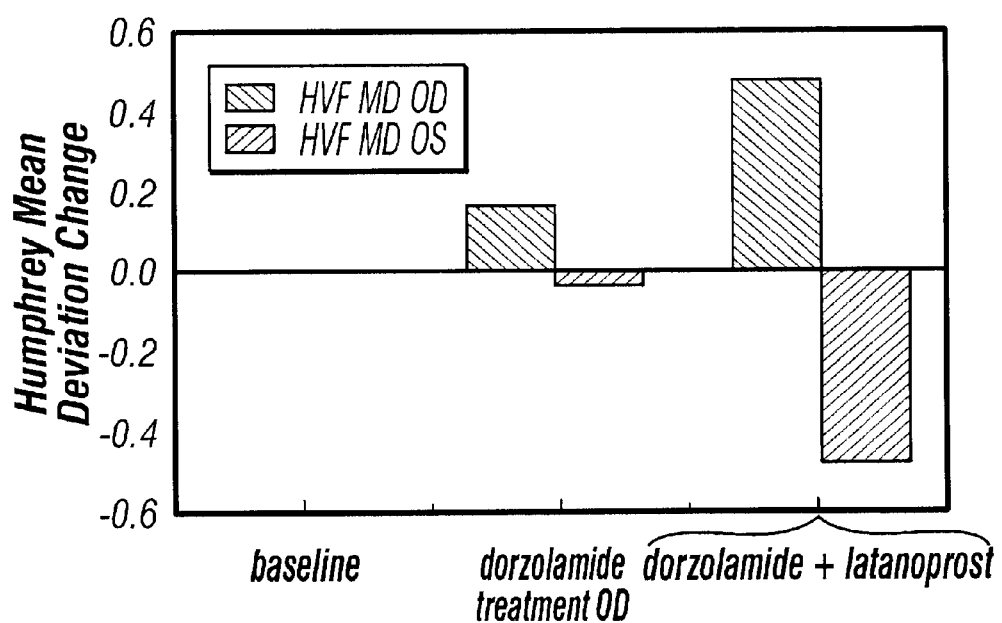
FIG. 4 is a graph showing changes from a baseline in visual function responses in both eyes as measured by Humphrey perimeter.

FIG. 4 shows the changes from baseline in visual function responses in both eyes as measured by the Humphrey perimeter. Visual fuiction change increased in the right eye (dorzolamide only) with no change in the (untreated) left eye on day 2, consistent with prior study results. On day 3, however, when both eyes demonstrated a significant intraocular pressure reduction associated with bilateral latanoprost treatment, visual function had increased 3-fold in the TCAI plus latanoprost-treated right eye, and actually diminished to a comparable extent in the eye receiving latanoprost only. These data illustrate dramatically a disproportionate synergistic effect of an independent intraocular pressure reducing drug (latanoprost) to the incremental positive effect of dorzolamide on retinal light sensitivity— even when the cotherapeutic ocular hypotensive agent actually reduced visual function when used in the absence of the TCAI.

EXAMPLE 3
(Clinical Response to Cotherapy with Dorzolamide Plus Carteolol in a 67 Year-old Female with an Acute Macular Disorder)

A 67 year old Caucasian female with mild myopia presented to an eye clinic for a scheduled follow-up visit. She had a two year history of central visual blurring in the left eye, maintaining Snellen acuities of 20/20 in the right eye and 20/30 in the left, and intraocular pressures in the mid-teens in both eyes. She had no prior history of ocular trauma, diabetes, or other manifest ocular disease, but her clinical record confirmed the presence of a symmetric myopic disc configuration and peripapillary atrophy in both eyes. In addition, stereoscopic examination at the time revealed an idiopathic macular epiretinal membrane in the left eye, with mild drusen associated with irregularities of the retinal pigment epithelium in the papillomacular bundle of both eyes. Serial examination over the ensuing two-year period demonstrated relative stability of these findings, and an absence of any demonstrable pericentral visual field loss on Humphrey 30-2 thresholding perimetry in either eye.

Examination of both eyes yielded normal slit lamp findings, normal pupil reactions and ocular motility. The acuities were 20/25 in the right and 20/30 in the left, and the patient was aware of decreased central vision in her previously asymptomatic right eye. Ophthalmoscopic examination of the left eye confirmed the presence of the peripapillary changes and epiretinal membrane noted previously. The right eye showed, in addition to the changes noted on the prior photographic record, temporal extension of the retinal pigment ipithelial mottling just nasal to the fovea centralis. There was no associated hemorrhage, choroidal neovascular membrane, or edema present, although there were additional drusen.

Figure 5:
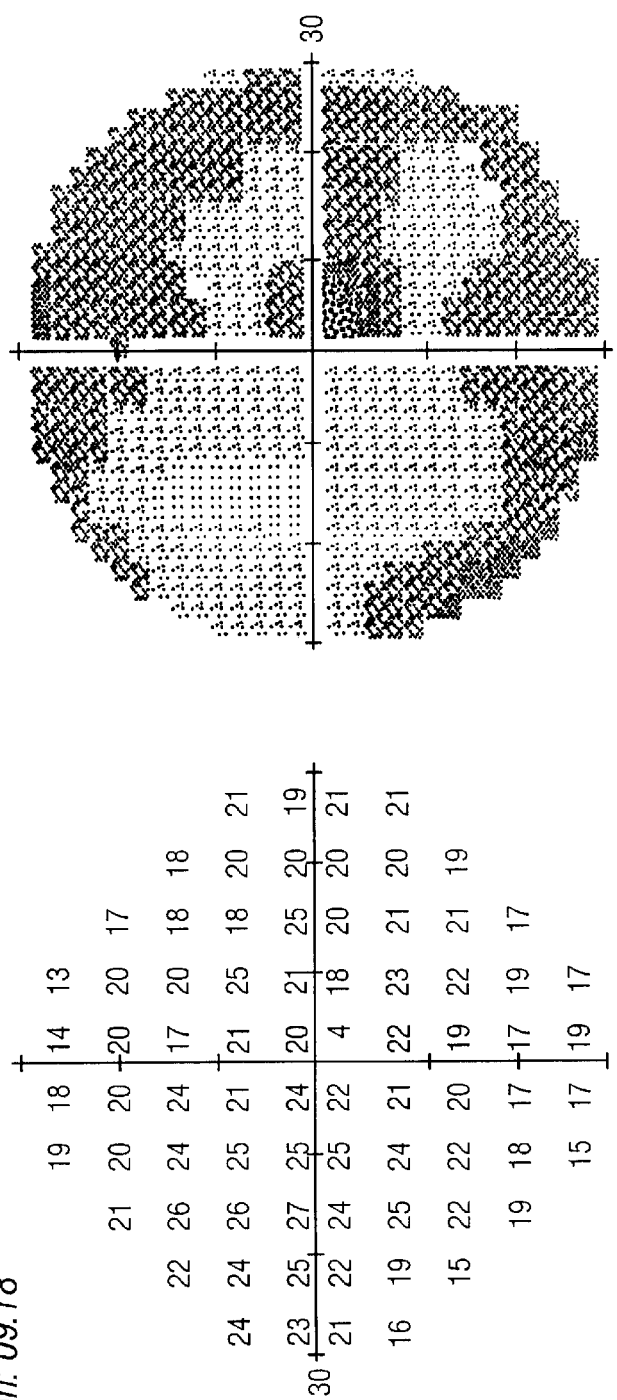
FIG. 5 illustrates a Humphrey 30-2 visual field report of the patient in Example 3.
Figure 6:
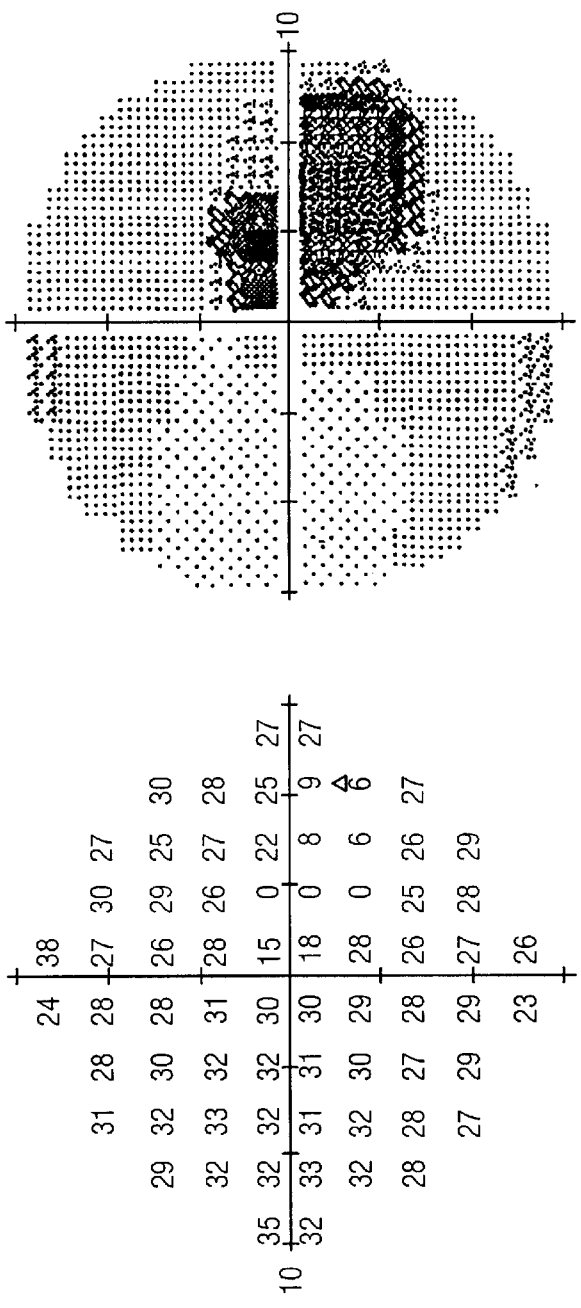
FIG. 6 illustrates a 10-degree visual field of the same patient at the start of the test in Example 3.

Humphrey 30-2 visual fields were obtained. A dense pericentral scotoma was present in the right eye (FIG. 5) which was not present in any of her prior visual field exams (FIG. 7). A detailed 10-degree visual field was immediately ordered (FIG. 6) revealing a highly reproducible, non-neurologic, non-glaucomatous macular scotoma in a location pathophysiologically consistent with her zone of ophthalmoscopic change. The visual field defect did not respect the horizontal meridian, was not contiguous with the physiologic blind spot, and was severe in 9 contiguous loci, including both the superior and inferior temporal perifoveolar zones, but was immediately surrounded by areas of near-normal retinal sensitivity to light. These changes were consistent with early evolving age-related macular degeneration in the right eye.

The patient was placed on a daily regimen of carteolol 0.5% (a noncardioselective topical beta adrenergic antagonist with intrinsic sympathomimetic activity) and dorzolamide 2% (a topical carbonic anhydrase inhibitor) twice daily in the right eye with the intent of enhancing ocular perfusion. She was scheduled to return for repeat detailed 10-degree visual field assessment once this treatment regimen had been maintained for six weeks.

Figure 8:
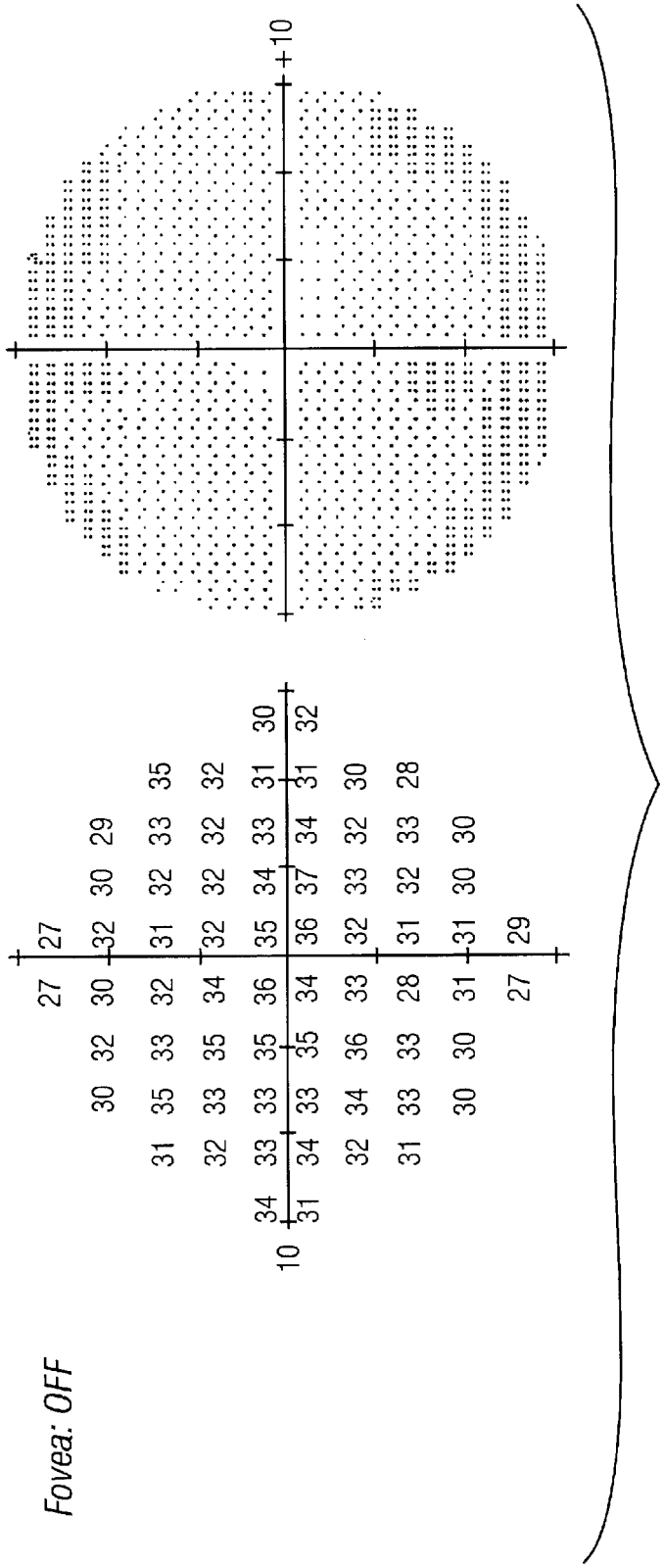
FIG. 8 shows the follow up visual field of the patient of Example 3, after treatment with the method and a composition of the present invention.

The follow-up visual field obtained within eleven weeks is shown in FIG. 8. The dense scotoma in the temporal macula had completely resolved, and the adjacent macular threshold values in all sectors of the visual field were significantly improved. The Snellen acuity in the treated right eye had returned to 20/20; the untreated left eye remained 20/30. Three months later the treated eye was still clear.

This example represents the first use of the combination of a topical carbonic anhydrase inhibitor (CAI) and non-CAI aqueous suppressant for the treatment of emerging age-related macular degeneration through the enhancement of ocular perfusion and visual function, according to the principles of the present invention. This novel combination therapy for apparent early-to-moderate macular degeneration was dramatically effective in this patient. This reversal of a new, dense, highly reproducible macular visual defect which arose concomitantly with a spatially-corresponding, new ophthalmoscopically-confirmed extension of macular degenerative fundus change, in a perimetrically-experienced subject with previously normal fields, is extraordinary.

EXAMPLE 4
(Clinical Response to Cotherapy with Dorzolamide Plus Timolol in a 79 Year-old Female with a Chronic Macular Disorder)

Figure 9:
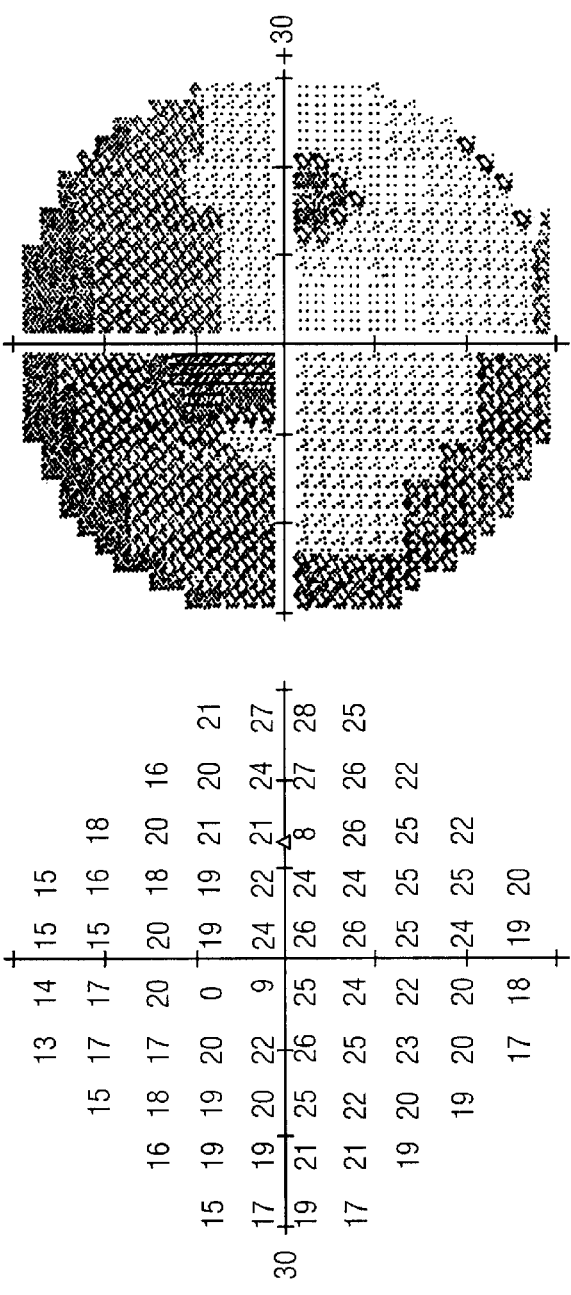
FIG. 9 shows the right visual field of the patient in Example 4 prior to treatment.

Shortly after the patient outcome described in Example 3, combination therapy was applied to another patient with a quite different history. This 79 year old female presented to an eye clinic. She had intraocular pressures of 16 mm Hg in the right eye and 14 mm Hg in the left. Despite having undergone cataract surgery in the right eye years earlier, the patient had a visual acuity of 20/400 in the right eye, with an acuity of 20/30 attributable to mild macular degeneration and cataract in the left eye. Ophthalmoscopic examination in the right eye revealed multiple drusen and scarring in the macular zone of the right eye, extending from the inferotemporal aspect of the macula into the fovea centralis. Visual fields were obtained immediately, and the patient proved to be highly reliable, with very few fixation losses or false positive or negative testing errors. Her left visual field was normal, but the right demonstrated a dense pericentral scotoma (FIG. 9) corresponding to the zone of macular scarring noted ophthalmoscopically.

The patient was placed on a twice-daily regimen of 2% dorzolamide plus timolol 0.5% in the right eye. She returned 12 weeks later for repeat visual field testing. Her intraocular pressures were 11 mm Hg in the right eye and 12 mm Hg in the left, representing a >30% reduction in pressure from the previously normal level in the right eye. Her visual acuity was unchanged in the left eye, and improved to 20/200 in the right.

Figure 10:
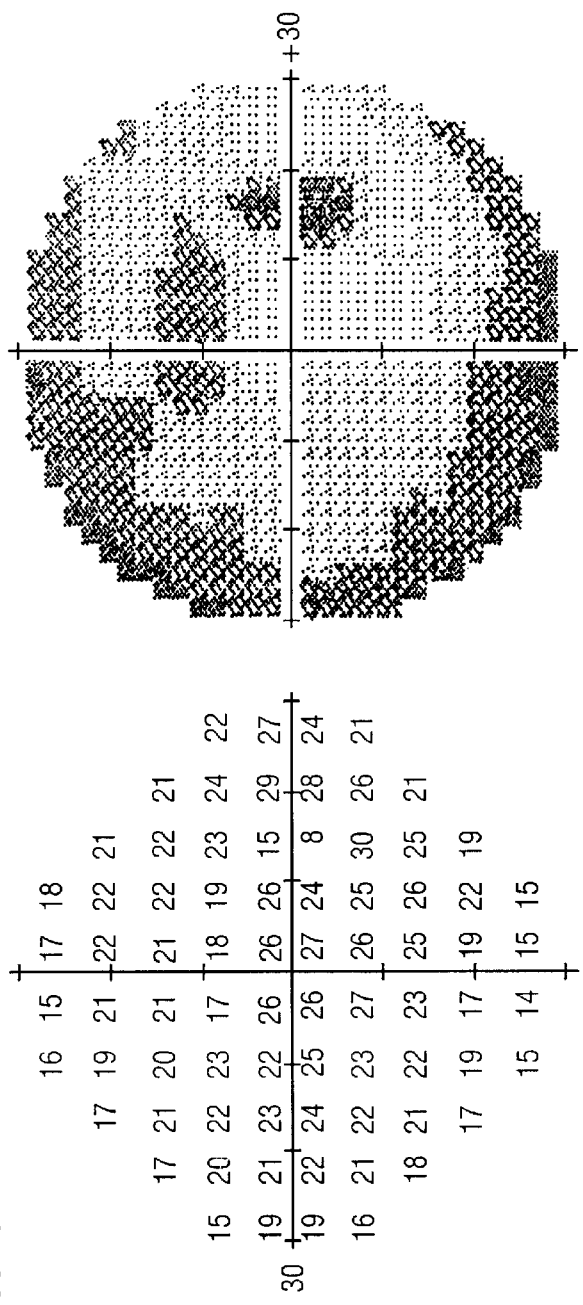
FIG. 10 illustrates the right visual field of the patient in Example 4 after treatment with the method and another composition of the present invention.

Most remarkably, despite her retained scarring in the perimacular zone on ophthalmoscopy, her retinal sensitivity to light had increased over 10,000-fold in the region associated with the old retinal scar according to the logarithmic scale of the Humphrey perimeter (FIG. 10). The anatomy of the retina was of course still distorted, accounting for her only marginal Snellen acuity improvement. However, the previously dysfunctional retinal tissue within the degenerative macula now appeared to be generating appropriate neural responses to local light stimuli. The patient was subjectively aware of this visual improvement.

The above examples demonstrate the apparent ability of cotherapy of TCAI with a variety of different independent pharmacologic ocular hypotensive agents to generate remarkable improvements in central retinal light sensitivity in normal, acutely diseased, and chronically diseased eyes. The effect is consistent with that hypothesized on the basis of the detailed analysis of the placebo-controlled double-masked crossover study described at the beginning of this summary.

The carbonic anhydrase inhibitor may be administered as a 0.01–5%, preferably a 0.5 to 2% solution or suspension and the ocular hypotensive agent as a 0.001% to 6.0% solution or suspension in an ophthalmologically acceptable carrier. Such agents include, but should not be limited to beta blockers (betaxolol, timolol, optipranolol, levobunolol, metapranolol, carteolol, and the like), miotic agents (pilocarpine, carbachol, phospholine iodide, and the like), adrenergic agonists (iopidine, brimonidine, epinephrine, dipivephrin, and the like), prostaglandin derivatives (latanoprost and the like), and related compounds directed toward the reduction of intraocular pressure, plus agents effective in the enhancement of carotid perfusion pressure, including a range of oral and sublingual systemic drugs intended to improve cardiac contractility or decrease carotid or ophthalmic arterial vascular resistance.

Although the invention has been described with reference to specific embodiments, this description is not meant to be construed in a limited sense. Various modifications of the disclosed embodiments, as well as alternative embodiments of the inventions will become apparent to persons skilled in the art upon the reference to the description of the invention. It is, therefore, contemplated that the appended claims will cover such modifications that fall within the scope of the invention.

I claim:

1. A composition for treating macular disorders comprising a pharmocologically effective amount of a carbonic anhydrase inhibitor in combination with a pharmocologically effective amount of an ocular hypotensive agent.

2. The composition of claim 1 wherein said carbonic anhydrase inhibitor is selected from the group consisting of dorzolamide and brinzolamide and their mixtures.

3. The composition of claim 1 wherein said ocular hypotensive agent is selected from the group consisting of beta blockers, miotic agents, adrenergic agonists, prostaglandin derivatives, carotid perfusion pressure agents, and oral and sublingual systemic agents to improve cardiac contractility or decrease carotid or ophthalmic arterial vascular resistance.

4. The composition of claim 1 wherein said carbonic anhydrase inhibitor is dorzolamide.

5. The composition of claim 1, wherein the concentration of said carbonic anhydrase inhibitor is 0.01% to 5% dorzolamide weight/volume and the concentration of said ocular hypotensive agent is 0.001% to 6% weight/volume.

6. A composition for increasing retinal blood flow comprising at least one carbonic anhydrase inhibitor and at least one adrenergic agonist, prostaglandin derivative, or miotic agent.

7. The composition of claim 6, wherein the composition further comprises a beta blocker.

8. The composition of claim 6, wherein the composition is an ophthalmic preparation.

9. The composition of claim 6, wherein the composition comprises a solution, gel, semisolid, suspension, metered dose device, transdermal patch or film.

10. The composition of claim 8, wherein said ophthalmic preparation comprises a carbonic anhydrase inhibitor at a concentration of about 0.01% weight/volume to about 5% weight/volume.

11. The composition of claim 6, wherein said ophthalmic preparation includes an adrenergic agonist at a concentration of about 0.001% weight/volume to about 6.0% weight/volume.

12. The composition of claim 6, wherein said ophthalmic preparation includes a miotic agent at a concentration of about 0.001% weight/volume to about 6.0% weight/volume.

13. The composition of claim 6, wherein said ophthalmic agent includes a prostaglandin derivative at a concentration of about 0.001% weight/volume to about 6.0% weight/volume.

14. The composition of any one of claims 7, 11, 12, or 13 further comprising a carbonic anhydrase inhibitor at a concentration of about 0.01% weight/volume to about 5% weight/volume.

15. The composition of claim 6, wherein the composition comprises at least one carbonic anhydrase inhibitor and at least one adrenergic agonist.

16. The composition of claim 15, wherein the adrenergic agonist is iopidine, brimonidine, epinephrine or dipivephrin.

17. The composition of claim 6, wherein the carbonic anhydrase inhibitor is dorzolamide, brinzolamide, acetazolamide, methazolamide or 6-hydroxy-2-benzothiazolesulfonamide.

18. The composition of claim 16, wherein the composition comprises dorzolamide and brimonidine.

19. The composition of claim 6, wherein the prostaglandin derivative is latanoprost.

20. The composition of claim 19, wherein the composition comprises dorzolamide and latanoprost.

21. The composition of claim 19, wherein the composition comprises brinzolamide and latanoprost.

22. The composition of claim 6, wherein the miotic agent is pilocarpine, carbichol or phospholine iodide.

23. The composition of claim 22, wherein the composition comprises dorzolamide and pilocarpine.

24. The composition of claim 22, wherein the composition comprises brinzolamide and pilocarpine.

25. A method of improving the health of the optic nerve comprising administering to a patient at least one carbonic anhydrase inhibitor and at least one ocular hypotensive agent or inotropic agent in an amount sufficient to improve the health of the optic nerve.

26. A method of treating a retinal disorder comprising administering to a patient in need of retinal therapy at least one carbonic anhydrase inhibitor and at least one ocular hypotensive agent or inotropic agent in an amount sufficient to treat the disorder.

27. A method of treating macular disorders comprising applying a composition of carbonic anhydrase inhibitor in combination with an ocular hypotensive agent in an amount sufficient to improve visual function.

28. The method of claim 27 wherein said carbonic anhydrase inhibitor is selected from the group consisting of dorzolamide and brinzolamide and their mixtures.

29. The method of claim 27 wherein said ocular hypotensive agent is selected from the group consisting of beta blockers, miotic agents, adrenergic agonist, prostaglandin derivatives, carotid perfusion pressure agents, and oral and sublingual systemic agents to improve cardiac contractility or decrease carotid or ophthalmic arterial vascular resistance.

30. The method of claim 27 wherein said carbonic anhydrase inhibitor is dorzolamide.

31. The method of claim 27 wherein the concentration of said carbonic anhydrase inhibitor is 0.01% to 5% dorzolamide weight/volume and the concentration of said ocular hypotensive agent is 0.001% to 6% weight/volume.

32. A method of increasing retinal blood flow comprising administering to a patient at least one carbonic anhydrase inhibitor and at least one ocular hypotensive agent or inotropic agent in an amount sufficient to increase retinal blood flow.

33. The method of claim 32, wherein a carbonic anhydrase inhibitor and an ocular hypotensive or inotropic agent are formulated in an ophthalmic preparation for topical application to the eye.

34. The method of claim 33, wherein the carbonic anhydrase inhibitor and ocular hypotensive or inotropic agent are administered in the same composition.

35. The method of claim 32, wherein the carbonic anhydrase inhibitor is acetazolamide, methazolamide, dorzolamide, brinzolamide, 6-hydroxy-2-benzothiazolesulfonamide, an ester of 6-hydroxy-2-benzothiazolesulfonamide, an ester of 5-hydroxy-2-benzothiazolesulfonamide, a thiophene sulfonamide or an aromatic sulfonamide with a saturated heterocycle fused thereto.

36. The method of claim 32, wherein the ocular hypotensive agent or inotropic agent is a beta-blocker, adrenergic agonist, miotic agent, prostaglandin derivative, or carotid perfusion pressure agent.

37. The method of claim 36, wherein the ocular hypotensive agent or inotropic agent is an oral and sublingual systemic agent to improve cardiac contractility or decrease carotid or ophthalmic arterial vascular resistance.

38. The method of claim 36 wherein at least one carbonic anhydrase inhibitor and at least one beta-blocker are administered.

39. The method of claim 38, wherein the beta blocker is timolol, betaxolol, optipranolol, levobunolol, metapranolol or carteolol.

40. The method of claim 39, wherein the carbonic anhydrase inhibitor is dorzolamide, brinzolamide, acetazolamide, methazolamide or 6-hydroxy-2-benzothiazolesulfonamide.

41. The method of claim 40, wherein dorzolamide and timolol are administered.

42. The method of claim 40, wherein brinzolamide and timolol are administered.

43. The method of claim 40, wherein dorzolamide and betaxolol are administered.

44. The method of claim 40, wherein brinzolamide and betaxolol are administered.

45. The method of claim 40, wherein dorzolamide and levobunolol are administered.

46. The method of claim 40, wherein brinzolamide and levobunolol are administered.

47. The method of claim 40, wherein dorzolamide, betaxolol and timolol are administered.

48. The method of claim 40, wherein brinzolamide, betaxolol and timolol are administered.

49. The method of claim 36, wherein at least one carbonic anhydrase inhibitor and at least one adrenergic agonist is administered.

50. The method of claim 49, wherein the adrenergic agonist is iopidine, brimonidine, epinephrine or dipivephrin.

51. The method of claim 50, wherein the carbonic anhydrase inhibitor is dorzolamide, brinzolamide, acetazolamide, methazolamide or 6-hydroxy-2-benzothiazolesulfonamide.

52. The method of claim 51, wherein dorzolamide and brimonidine are administered.

53. The method of claim 51, wherein brinzolamide and brimonidine are administered.

54. The method of claim 51, wherein dorzolamide and iopidine are administered.

55. The method of claim 51, wherein brinzolamide and iopidine are administered.

56. The method of claim 36, wherein at least one carbonic anhydrase inhibitor and at least one miotic agent are administered.

57. The method of claim 56, wherein the miotic agent is pilocarpine, carbachol, or phospholine iodide.

58. The method of claim 57, wherein the carbonic anhydrase inhibitor is dorzolamide, brinzolamide, acetazolamide, methazolamide or 6-hydroxy-2-benzothiazolesulfonamide.

59. The method of claim 58, wherein dorzolamide and pilocarpine are administered.

60. The method of claim 58, wherein brinzolamide and pilocarpine are administered.

61. The method of claim 58, wherein dorzolamide and carbachol are administered.

62. The method of claim 58, wherein brinzolamide and carbachol are administered.

63. The method of claim 36, wherein at least one carbonic anhydrase inhibitor and at least one prostaglandin derivative are administered.

64. The method of claim 63, wherein the prostaglandin derivative is latanoprost.

65. The method of claim 64, wherein the carbonic anhydrase inhibitor is dorzolamide, brinzolamide, acetazolamide, methazolamide or 6-hydroxy-2-benzothiazolesulfonamide.

66. The method of claim 65, wherein dorzolamide and latanoprost are administered.

67. The method of claim 65, wherein brinzolamide and latanoprost are administered.

68. The method of claim 32, wherein a carbonic anhydrase inhibitor is an aromatic sulfonamide with a saturated heterocycle fused thereto, having the structural formula:

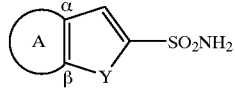

wherein A together with the two carbon atoms denoted as α and β is the group:

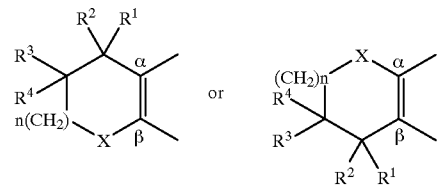

wherein:

X is —S—, —SO—, —SO$_2$— or —CH$_2$—;

Y is —S—, —O—, or —NR$^3$— wherein R$^3$ is hydrogen, C$_{1-3}$ alkyl, or benzyl;

n is 1 or 2;

R$^1$, R$^2$, R$^3$, R$^4$ are independently selected from:
(1) hydrogen,
(2) OR$^5$ wherein R$^5$ is:
  (a) hydrogen,
  (b) C$_{1-5}$ alkyl, either unsubstituted or substituted with —OH, or wherein R$^6$ and R$^7$ are independently hydrogen or C$_{1-5}$ alkyl, or joined together form a heterocycle with the nitrogen to which they are attached such as piperidino, morpholino, or piperazino,
  (c) C$_{1-5}$ alkanoyl, either unsubstituted or substituted with —OH, —NR$^6$R$^7$, —NH—COR$^8$ or —COR$^8$ wherein R$^8$ is —OH, —NR$^6$R$^7$ or C$_{1-5}$ alkoxy,
  (d) —CO—R$^9$, wherein R$^9$ is —NR$^6$R$^7$ or a 5- or 6-membered aromatic heterocycle such as pyridyl, imidazolyl, pyrazinyl, thiazolyl, thienyl, or oxazolyl,
(3) —NR R ,
(4) —NHR$^{10}$ wherein R$^{10}$ is:
  (a) —SO$_2$NR$^6$R$^7$,
  (b) —SO$_2$R$^{11}$, wherein R$^{11}$ is C$_{1-5}$ alkyl, or
  (c) —CONR$^6$R$^7$,
(5) C$_{1-5}$ alkyl, either unsubstituted or substituted with
  (a) —OR$^5$,
  (b) —CN,
  (c) —NR$^6$R$^7$, or
  (d) —COR$^8$,
(6) —SO$_2$R$^{11}$,
(7) —SO$_2$NR$^6$R$^7$, or
(8) -halo, such as chloro, bromo or fluoro;
(9) R$^1$ and R$^3$, or R$^2$ and R$^4$ taken together represent a double bond;
(10) R$^1$ and R$^2$, or R$^3$ and R$^4$ taken together represent
  (a) =O, or
  (b) =NOR$^{12}$, wherein R$^{12}$ is hydrogen or C$_{1-3}$ alkyl; and one of the —CH$_2$— groups of —(CH$_2$)$_n$— can be substituted with —COR$^8$, —CH$_2$R$^8$, or —CH$_2$COR$^8$.

69. The method of claim 68, wherein Y is —S, X is —S—or —SO$_2$—, n is 1, R$^2$ is hydrogen, R$^3$ and R$^4$ are hydrogen or C$_{1-5}$ alkyl and R$^1$ is —OH, —CH$_2$OH or —NR$^6$R$^7$.

70. The method of claim 69, wherein the aromatic sulfonamide with saturated heterocycle fusion is selected from the group consisting of:

5,6-dihydro-4-ethylamino-6-methyl-4H-thieno[2,3-b]thiopyran-2-sulfonamide-7,7-dioxide, its (-)-trans enantiomer, 5,6-dihydro-4-(2-methylpropylamino)-6-methyl-4H-thieno[2,3-b]thiopyran-2-sulfonamide-7,7-dioxide, its (-)-trans enantiomer, 5,6-dihydro-6,6-dimethyl-4-ethylamino-4H-thieno[2,3-b]thiopyran-2-sulfonamide-7,7-dioxide, 5,6-dihydro-5-(3-dimethylaminomethyl-4-hydroxybenzyl)-4H-thieno[2,3-b]thiopyran-2-sulfonamide-7,7-dioxide, and 5,6-dihydro-6-(3-dimethylaminomethyl-4-hydroxyphenyl)-4H-thieno[2,3-b]thiopyran-2-sulfonamide-7,7-dioxide.

71. The method of claim 32, wherein a carbonic anhydrase inhibitor is an aromatic sulfonamide with a saturated heterocycle fusion having the structural formula:

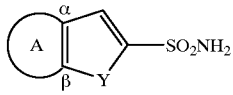

wherein

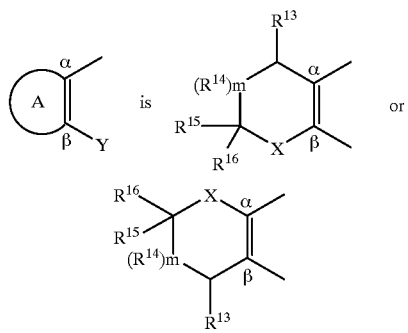

wherein:

X is —S—, —$SO_2$—, or —$CH_2$—;

Y is —S—, —O—, or —$NR^{19}$, wherein $R^{19}$ is H, $C_{1-3}$ alkyl or benzyl, m is 0 or 1, $R^{13}$ is
(1) hydrogen,
(2) phenyl either unsubstituted or substituted with one or more of
(a) hydroxy,
(b) $C_{1-3}$ alkoxy,
(c) $R^{17}R^{18}N$—$C_{1-5}$ alkyl wherein $R^{17}$ and $R^{18}$ are independently selected from:
(i) hydrogen or
(ii) $C_{1-5}$ alkyl, or taken together with the nitrogen to which they are attached form a heterocycle such as morpholine, piperidine, pyrrolidine, or piperazine,
(3) —OH,
(4) =O; or
(5) —$NR^{17}R^{18}$, $R^{14}$ is
(1) hydrogen,
(2) —CN,
(3) phenyl-$C_{1-3}$ alkyl, wherein the phenyl is either unsubstituted or substituted with one or more of
(a) hydroxy,
(b) $C_{1-3}$ alkoxy, or
(c) $R^{17}R^{18}N$—$C_{1-5}$ alkyl;

$R^{15}$ is
(1) hydrogen,
(2) $C_{1-5}$ alkyl,
(3) phenyl-$C_{1-3}$ alkyl, wherein the phenyl is either unsubstituted or substituted with one or more of:
(a) hydroxy,
(b) $C_{1-3}$ alkoxy, or
(c) $R^{17}R^{18}N$—$C_{1-3}$ alkyl;
(4) phenyl either unsubstituted or substituted with one or more of:
(a) hydroxy,
(b) $C_{1-3}$ alkoxy, or
(c) $R^{17}R^{18}N$—$C_{1-3}$ alkyl, or
(d) halo, such as chloro or fluoro
(5) aromatic heterocycle of 5 or 6 members such as furyl, pyridyl, or thienyl either unsubstituted or substituted with $R^{17}R^{18}N$—$C_{1-3}$ alkyl,
(6) —$NR^{17}R^{18}$, and
(7) $C_{2-5}$ alkyl substituted with —$NR^{17}R^{18}$;

$R^{16}$ is
(1) hydrogen,
(2) $C_{1-3}$ alkyl, or
(3) $C_{1-3}$ alkylene, such as methylene;

with the proviso that if $R^{13}$ is other than phenyl or substituted phenyl, and $R^{14}$ is hydrogen, one of $R^{15}$ and $R^{16}$ is other than hydrogen.

72. The method of claim 71, wherein X is —$SO_2$—; $R^{13}$ is hydrogen or —$NR^{17}R^{18}$; $R^{14}$ is hydrogen; $R^{16}$ is hydrogen or $C_{1-3}$ alkyl; and $R^{15}$ is $C_{1-3}$ alkyl or phenyl substituted with hydroxy and/or $R^{17}R^{18}N$—$C_{1-3}$ alkyl.

73. The method of claim 32, wherein a carbonic anhydrase inhibitor is a thiophene sulfonamide having the structure:

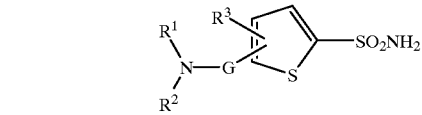

wherein:

$R^1$ is
(1) H,
(2) $C_{14}$ alkyl, or
(3) $C_{24}$ alkyl substituted with
(a) OH,
(b) halogen,
(c) $C_{1-4}$ alkoxy, or
(d) C(=O)$R^7$, $R^2$ is
(1) H,
(2) $C_{1-8}$ alkyl,
(3) $C_{2-8}$ alkyl substituted with
(a) —OH,
(b) —$NR^5R^6$,
(c) halogen
(d) $C_{1-4}$ alkoxy, or
(e) C(=O)$R^7$,
(4) $C_{3-7}$ alkenyl unsubstituted or substituted with
(a) OH,
(b) $NR^5R^6$, or
(c) $C_{1-4}$ alkoxy,
(5) $C_{3-7}$ alkynyl, unsubstituted or substituted with
(a) OH,
(b) $NR^5R^6$, or
(c) $C_{1-4}$ alkoxy,
(6) $C_{1-3}$ alkyl substituted with
(a) phenyl, or
(b) heteroaryl, unsubstituted or substituted with
(i) OH, (ii) $(CH_2)_nNR^5R^6$,
(iii) halogen,
(iv) $C_{1-4}$ alkoxy,
(v) $C_{1-4}$ haloalkoxy,
(vi) $C(=O)R^7$,
(vii) $S(=O)_mR^8$, or
(viii) $SO_2NR^5R^6$;
wherein m is 0–2 and n is 0–2,
(7) $C_{2-4}$ alkoxy substituted with
  (a) $NR^5R^6$,
  (b) halogen
  (c) $C_{1-4}$ alkoxy, or
  (d) $C(=O)R^7$;
(8) phenyl, or
(9) heteroaryl, unsubstituted or substituted with
  (a) OH,
  (b) $(CH_2)_nNR^5R^6$,
  (c) halogen,
  (d) $C_{1-4}$ alkoxy,
  (e) $C_{1-4}$ haloalkoxy,
  (f) $C(=O)R^7$,
  (g) $S(=O)_mR^8$, or
  (h) $SO_2NR^5R^6$;
wherein m is 0–2 and n is 0–2,
with the proviso that $R^1$ and $R^2$ cannot both be H, or $R^1$ and $R^2$ can form a saturated ring of 5 or 6 atoms selected from O, S, C, or N, said ring being unsubstituted or substituted on C with
(1) OH,
(2) $NR^5R^6$,
(3) halogen,
(4) $C_{1-4}$ alkoxy,
(5) $C(=O)R^7$,
(6) $C_{1-6}$ alkyl,
(7) $C_{1-6}$ alkyl substituted with
  (a) OH,
  (b) $NR^5R^6$,
  (c) halogen,
  (d) $C_{1-4}$ alkoxy,
  (e) $C(=O)R^7$ or
substituted on N with
(1) $NR^5R^6$,
(2) $C_{1-4}$ alkoxy,
(3) $C(O)R^7$
(4) $C_{1-6}$ alkyl,
(5) $C_{1-6}$ alkyl substituted with
  (a) OH,
  (b) $NR^5R^6$,
  (c) halogen,
  (d) $C_{1-4}$ alkoxy, or
  (e) $C(=O)R^7$;
$R^3$ is
(1) H,
(2) halogen,
(3) $C_{1-4}$ alkyl,
(4) $C_{1-8}$ alkoxy,
(5) $C_{1-8}$ alkylthiol,
(6) $C_{2-8}$ alkoxy substituted with
  (a) OH,
  (b) $NR^5R^6$,
  (c) halogen,
  (d) $C_{1-4}$ alkoxy,
  (e) $C(=O)R^7$,
(7) $C_{14}$ alkyl substituted with $R^4$,
(8) $R^1$ and $R^2$ form a ring of 5 to 7 members, said ring being unsubstituted or substituted with $R^4$;
$R^4$ is (1) OH,
(2) $C_{1-4}$ alkyl unsubstituted or substituted with
  (a) OH
  (b) $NR^5R^6$,
  (c) halogen,
  (d) $C_{1-4}$ alkoxy, or
  (e) $C(=O)R^7$,
(3) $C_{1-4}$ alkoxy,
(4) $C_{2-4}$ alkoxy substituted with
  (a) OH,
  (b) $NR^5R^6$,
  (c) halogen,
  (d) $C_{1-4}$ alkoxy or
  (e) $C(=O)R^7$,
(5) $NR^5R^6$,
(6) phenyl, or
(7) heteroaryl, unsubstituted or substituted with
  (a) OH,
  (b) $(CH_2)_nNR^5R^6$,
  (c) halogen,
  (d) $C_{1-4}$ alkoxy,
  (e) $C_{1-4}$ haloalkoxy,
  (f) $C(=O)R^7$,
  (g) $S(=O)_mR^8$, or
  (h) $SO_2NR^5R^6$,
wherein m is 0–2 and n is 0–2;
with the proviso that when $R^3$ is in the 4 position and is H or halogen then $R^1$ and $R^2$ are not
(1) H,
(2) $C_{1-6}$ alkoxy substituted with
  (a) OH,
  (b) $C_{1-6}$ alkoxy,
  (c) $C_{2-6}$ alkoxycarbonyl, or
(3) joined to form a 5, 6, or 7 member ring, saturated or unsaturated, comprised of atoms selected from C, O, S, N in which N, when saturated is substituted with H or $C_{1-6}$ alkyl or in which C is substituted with $C_{1-6}$ alkyl, $C_{1-6}$ alkoxy or OH;
and when $R^3$ is in the 5 position and is H, Cl, Br or $C_{1-3}$ alkyl then $R^1$ and $R^2$ are not H or $C_{1-4}$ alkyl;
$R^5$ and $R^6$ are the same or different and are
(1) H,
(2) $C_{1-4}$ alkyl,
(3) $C_{2-4}$ alkyl substituted with
  (a) OH,
  (b) halogen,
  (c) $C_{1-4}$ alkoxy, or
  (d) $C(=O)R^7$,
(4) $C_{1-4}$ alkoxy,
(5) $C_{2-4}$ alkoxy substituted with
  (a) OH,
  (b) halogen,
  (c) $C_{1-4}$ alkoxy, or
  (d) $C(=O)R^7$,
(6) $C_{3-7}$ alkenyl unsubstituted or substituted with
  (a) OH,
  (b) $NR^5R^6$, or
  (c) $C_{1-4}$ alkoxy,
(7) $C_{3-7}$ alkynyl unsubstituted or substituted with
  (a) OH,
  (b) $NR^5R^6$, or
  (c) $C_{1-4}$ alkoxy,
(8) $C_{1-2}$ alkyl $C_{3-5}$ cycloalkyl or
(9) $R^5$ and $R^6$ form a ring of 5 or 6 atoms selected from O, S, C, and N, said ring being unsubstituted or substituted
on C with (a) OH,
(b) (=O)
(c) halogen,
(d) $C_{1-4}$ alkoxy,
(e) $C(=O)R^7$,
(f) $C_{1-6}$ alkyl,
(g) $C_{1-6}$ alkyl substituted with
   (i) OH,
   (ii) halogen,
   (iii) $C_{1-4}$ alkoxy,
   (iv) $C(=O)R^7$,
or on N with
(a) $C_{1-4}$ alkoxy,
(b) $C(=O)R^7$,
(c) $S(=O)_m R^8$,
(d) $C_{1-6}$ alkyl, or
(e) $C_{2-6}$ alkyl substituted with
   (i) OH,
   (ii) halogen,
   (iii) $C_{1-4}$ alkoxy,
   (iv) $C(=O)R^7$,
or on S with (=O)m wherein m is 0–2;
$R^7$ is
(1) $C_{1-8}$ alkyl,
(2) $C_{1-8}$ alkyl substituted with
   (a) OH,
   (b) $NR^5R^6$,
   (c) halogen,
   (d) $C_{1-4}$ alkoxy, or
   (e) $C(=O)R^9$,
(3) $C_{1-4}$alkoxy,
(4) $C_{2-4}$ alkoxy substituted with
   (a) OH,
   (b) $NR^5R^6$,
   (c) halogen, or
   (d) $C_{1-4}$ alkoxy, or
(5) $NR^5R^6$;
$R^8$ is
(1) $C_{1-4}$alkyl,
(2) $C_{2-4}$ alkyl substituted with
   (a) OH,
   (b) $NR^5R^6$,
   (c) halogen,
   (d) $C_{1-4}$ alkoxy, or
   (e) $C(=O)R^7$;
$R^9$ is
(1) $C_{1-4}$alkyl,
(2) $C_{1-4}$ alkoxy,
(3) amino,
(4) $C_{1-3}$ alkylamino or
(5) di-$C_{1-3}$ alkylamino, and
G is $C(=O)$ or $SO_2$.

74. The method of claim 73, wherein the thiophene sulfonamide is selected from the group consisting of
(+)-3,4-dihydro-4-ethylamino-2-methyl-4H-thieno[3,2-e]-1,2-thiazine-6-sulfonamide-1,1-dioxide, its HCl salt,
3,4-dihydro-4-methoxy-2-methyl-4H-thieno[3,2-e] -1,2-thiazine-6-sulfonamide-1,1-dioxide,
3,4-dihydro-2-methyl-4(2-methyl)propylamino-4H-thieno[3,2-e]-1,2-thiazine-6-sulfonamide-1,1-dioxide, its HCl salt,
3,4-dihydro-4-methoxy-2-[2-(4-morpholino)ethyl]-4H-thieno[3,2-e]-1,2-thiazine-6-sulfonamide-1,1-dioxide,
3,4-dihydro-4-ethylamino-2-allyl-4H-thieno[3,2-e]-1,2-thiazine-6-sulfonamide-1,1-dioxide,
3,4-dihydro-4-ethylamino-2-n-propyl-4H-thieno[3,2-e]-1,2-thiazine-6-sulfonamide-1,1-dioxide,
3,4-dihydro-4-ethylamino-2-(2-methoxyethyl)-4H-thieno[3,2-e]-1,2-thiazine-6-sulfonamide-1,1-dioxide, and
3,4-dihydro-4-hydroxy-2-[2-(4-morpholino)ethyl]-4H-thieno[3,2-e]-1,2-thiazine-6-sulfonamide-1,1-dioxide.

75. The method of claim 32, wherein a carbonic anhydrase inhibitor is an ester of 5-hydroxy-2-benzothiazolesulfonamide having the structural formula

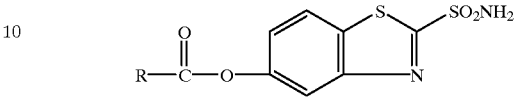

wherein R is
(1) $C_{1-18}$ alkyl,
(2) $C_{3-6}$ cycloalkyl,
(3) $C_{3-6}$ cycloalkyl $C_{1-18}$ alkyl,
(4) $C_{1-18}$ alkyl $C_{3-6}$ cycloalkyl,
(5) haloalkyl,
(6) aryl, unsubstituted or substituted with
   (a) $C_{1-10}$ alkyl, straight or branched,
   (b) halo selected from bromo, chloro and fluoro, or
   (c) alkoxy, selected from methoxy and ethoxy,
(7) arylalkyl, where alkyl is $C_{1-4}$ and aryl is unsubstituted or substituted with fluoro, chloro, bromo or $C_{1-3}$ alkyl,
(8) $C_{2-18}$ hydroxyalkyl,
(9) $C_{2-18}$ aminoalkyl,
(10) $C_{2-6}$ alkenyl,
(11) $C_{2-6}$ alkynyl, or
(12) aryl $C_{2-6}$ alkenyl.

76. The method of claim 75, wherein R is $C_{1-18}$ alkyl selected from the group consisting of methyl, ethyl, butyl, isopropyl, octyl, dodecyl and the like.

77. The method of claim 76, wherein R is butyl, straight or branched.

78. The method of claim 76, wherein R is 2,2-dimethylpropyl.

79. The method of claim 75, wherein R is $C_{3-6}$ cylcoalkyl selected from the group consisting of cyclopropyl, cyclobutyl, cyclopentyl and cyclohexyl.

80. The method of claim 75, wherein R is halo.

81. The method of claim 75, wherein R is cinnamyl.

82. The method of claim 75, wherein the ester of 5-hydroxy-2-benzothiazolesulfonamide is selected from the group consisting of:
(2-sulfamoyl-5-benzothiazolyl) benzoate,
(2-sulfamoyl-5-benzothiazolyl) propionate,
(2-sulfamoyl-5-benzothiazolyl) butyrate,
(2-sulfamoyl-5-benzothiazolyl) 2,2-dimethylpropionate,
(2-sulfamoyl-5-benzothiazolyl) cyclopentaneacetate,
(2-sulfamoyl-5-benzothiazolyl) phenylacetate,
(2-sulfamoyl-5-benzothiazolyl) cyclohexanecarboxylate,
(2-sulfamoyl-5-benzothiazolyl) acetate,
(2-sulfamoyl-5-benzothiazolyl) 2-(4-chlorophenyl) acetate,
(2-sulfamoyl-5-benzothiazolyl) 3-phenyl-2-propenoate,
(2-sulfamoyl-5-benzothiazolyl) 3-chloro-2,2-dimethylpropionate,
(2-sulfamoyl-5-benzothiazolyl) hexanoate,
(2-sulfamoyl-5-benzothiazolyl) trifluoroacetate,
(2-sulfamoyl-5-benzothiazolyl) succinate, (2-sulfamoyl-5-benzothiazolyl) acrylate,
(2-sulfamoyl-5-benzothiazolyl) 4-methylbenzoate,
(2-sulfamoyl-5-benzothiazolyl) 4-chlorobenzoate,
(2-sulfamoyl-5-benzothiazolyl) 2-methylpropionate,
(2-sulfamoyl-5-benzothiazolyl) octanoate, and
(2-sulfamoyl-5-benzothiazolyl) crotonate.

83. The method of claim 32, wherein a carbonic anhydrase inhibitor is an ester of 6-hydroxy-2-benzothiazolesulfonamide having the structure

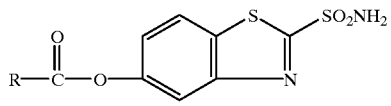

wherein R is
(1) $C_{1-18}$ alkyl,
(2) $C_{3-6}$ cycloalkyl,
(3) $C_{3-6}$ cycloalkyl $C_{1-18}$ alkyl,
(4) $C_{1-18}$ alkyl $C_{3-6}$ cycloalkyl,
(5) $C_{1-18}$ haloalkyl,
(6) aryl, unsubstituted or substituted with
  (a) $C_{1-10}$ alkyl, straight or branched,
  (b) halo selected from the group consisting of bromo, chloro, and fluoro, or
  (c) alkoxy,
(7) aryl alkyl, where the alkyl is a $C_{1-4}$ alkyl and the aryl is unsubstituted or substituted with fluoro, chloro, bromo or $C_{1-3}$ alkyl,
(8) $C_{2-18}$ hydroxyalkyl,
(9) $C_{2-18}$ amino alkyl,
(10) $C_{2-6}$ alkenyl,
(11) $C_{2-6}$ alkynyl, or
(12) aryl $C_{2-6}$ alkenyl.

84. The method of claim 83, wherein R is a $C_{1-18}$ alkyl selected from the group consisting of methyl, ethyl, butyl, isopropyl, octyl, dodecyl and the like.

85. The method of claim 83, wherein R is a $C_{3-6}$ cycloalkyl selected from the group consisting of cyclopropyl, cyclobutyl, cyclopentyl and cyclohexyl.

86. The method of claim 83, wherein R is aryl.

87. The method of claim 86, wherein the aryl is a cyclic or heterocyclic aromatic radical.

88. The method of claim 87, wherein the aromatic radical is selected from the group consisting of phenyl, naphthyl, pyridinyl, furanyl, thiophenyl and the like.

89. The method of claim 83, wherein the ester of 6-hydroxy-2-benzothiazolesulfonamide is selected from the group consisting of
(2-sulfamoyl-6-benzothiazolyl) benzoate,
(2-sulfamoyl-6-benzothiazolyl) propionate,
(2-sulfamoyl-6-benzothiazolyl) butyrate,
(2-sulfamoyl-6-benzothiazolyl) 2,2-dimethylpropionate,
(2-sulfamoyl-6-benzothiazolyl) octanoate,
(2-sulfamoyl-6-benzothiazolyl) dodecanoate,
(2-sulfamoyl-6-benzothiazolyl) 4,4-dimethylcyclohexanecarboxylate,
(2-sulfamoyl-6-benzothiazolyl) 3-chloro-2,2-dimethylpropionate,
(2-sulfamoyl-6-benzothiazolyl) 4-methylbenzoate,
(2-sulfamoyl-6-benzothiazolyl) 4-chlorobenzoate,
(2-sulfamoyl-6-benzothiazolyl) 4-methoxybenzoate,
(2-sulfamoyl-6-benzothiazolyl)2-(4-chlorophenyl) acetate,
(2-sulfamoyl-6-benzothiazolyl) 3-(4-ethylphenyl) propionate,
(2-sulfamoyl-6-benzothiazolyl) 3-hydroxy-2,2-dimethylpropionate,
(2-sulfamoyl-6-benzothiazolyl) 4-aminobutyrate HCl,
(2-sulfamoyl-6-benzothiazolyl) acrylate,
(2-sulfamoyl-6-benzothiazolyl) crotonate,
(2-sulfamoyl-6-benzothiazolyl) propiolate,
(2-sulfamoyl-6-benzothiazolyl) 3-phenyl-2-propenoate,
(2-sulfamoyl-6-benzothiazolyl) cyclopentaneacetate,
(2-sulfamoyl-6-benzothiazolyl) phenylacetate,
(2-sulfamoyl-6-benzothiazolyl) cyclohexanecarboxylate,
(2-sulfamoyl-6-benzothiazolyl) acetate.

90. The method of claim 32, wherein the patient has a retinal disorder having an etiology based at least in part on inadequate retinal blood flow.

91. The method of claim 90, wherein the retinal disorder comprises macular edema, macular degeneration, drusen or retinopathy of prematurity.

92. The method of claim 91, wherein the retinal disorder is macular degeneration.

93. The method of claim 92, wherein the macular degeneration is age-related macular degeneration.

94. The method of claim 91, wherein the retinal disorder is macular edema.

95. The method of claim 94, wherein the macular edema is with vascular leakage.

96. The method of claim 32, wherein the patient presents with normal visual function.

97. The method of claim 32, wherein administering improves visual function of the patient.

98. The method of claim 32, wherein the patient presents without ocular pathology.

99. The method of claim 32, wherein administering maintains retinal health of the patient.

100. The method of claim 32, wherein the carbonic anhydrase inhibitor is administered at a concentration of about 0.01% weight/volume to about 5.0% weight/volume.

101. The method of claim 100, wherein the carbonic anhydrase inhibitor is administered at a concentration of about 0.5% weight/volume to about 2.0% weight/volume.

102. The method of claim 38, wherein the beta-blocker is administered at a concentration of about 0.001% weight/volume to about 6.0% weight/volume.

103. The method of claim 49, wherein the adrenergic agent is administered at a concentration of about 0.001% weight/volume to about 6.0% weight/volume.

104. The method of claim 56, wherein the miotic agent is administered at a concentration of about 0.001% weight/volume to about 6.0% weight/volume.

105. The method of claim 63, wherein the prostaglandin derivative is administered at a concentration of about 0.001% weight/volume to about 6.0% weight/volume.

106. The method of any one of claims 102, 103, 104, or 105 wherein the carbonic anhydrase inhibitor is administered at a concentration of about 0.01% weight/volume to about 5.0% weight/volume.

* * * * *

UNITED STATES PATENT AND TRADEMARK OFFICE
CERTIFICATE OF CORRECTION

PATENT NO. : 6,313,155 B1
DATED : November 6, 2001
INVENTOR(S) : Sponsel

It is certified that error appears in the above-identified patent and that said Letters Patent is hereby corrected as shown below:

Column 18, claim 68,
Line 34, please delete "-NR R" and insert -- -NR$^6$R$^7$ -- therefor.

Column 21, claim 73,
Line 1, please delete "(CH$_2$),NR$^5$R$^6$" and insert -- (CH$_2$)$_n$NR$^5$R$^6$ -- therefor.
Line 44, please delete "C(O)R$^7$" and insert -- C(=O)R$^7$ -- therefor.
Line 64, please delete "C$_{14}$" and insert -- C$_{1-4}$ -- therefor.

Signed and Sealed this

Nineteenth Day of March, 2002

Attest:

JAMES E. ROGAN
Director of the United States Patent and Trademark Office

Attesting Officer